United States Patent
Minami et al.

(10) Patent No.: US 6,595,916 B2
(45) Date of Patent: Jul. 22, 2003

(54) ENDOSCOPE APPARATUS USING CURVATURE OF FIELD

(75) Inventors: Itsuji Minami, Omiya (JP); Hitoshi Miyano, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 133 days.

(21) Appl. No.: 09/778,074

(22) Filed: Feb. 7, 2001

(65) Prior Publication Data

US 2001/0016680 A1 Aug. 23, 2001

(30) Foreign Application Priority Data

Feb. 18, 2000 (JP) ........................................ 2000-041679
Mar. 27, 2000 (JP) ........................................ 2000-085972

(51) Int. Cl.[7] ............................................. A61D 1/045
(52) U.S. Cl. ........................ 600/167; 600/168; 359/648; 359/649; 359/650; 348/345; 348/349; 348/354
(58) Field of Search ................................ 600/160, 163, 600/167, 168, 176; 359/648–651; 348/345, 349, 354

(56) References Cited

U.S. PATENT DOCUMENTS 5,168,298 A * 12/1992 Hirai ........................... 396/121

FOREIGN PATENT DOCUMENTS

JP 4-194914 * 7/1992 ............ G03B/13/36

* cited by examiner

*Primary Examiner*—John Mulcahy
(74) *Attorney, Agent, or Firm*—Snider & Associates; Ronald R. Snider (57) ABSTRACT

This endoscope apparatus utilizes a phenomenon called "curvature of field" of a lens to satisfactorily bring a shape, into focus, of an object to be observed such as unevenness especially during enlargement in accordance with a shape of unevenness or the like of the object. For example, there is provided an objective lens group having two movable lenses, and variable-power is performed and field curvature characteristics are changed by moving these movable lenses. This change in the field curvature characteristics is performed by operating an image surface curving switch and driving the movable lenses through the use of an actuator or the like. Also, information on differences in height on the image central part to the peripheral part is operated from the amount of field curvature changed by the objective lens group to display the information on differences in height on the monitor. Further, the image information on the divided areas are compared, and when the entire image is in focus, a static image is formed and the information on differences in height is displayed.

9 Claims, 11 Drawing Sheets

(DISPLAY IN CONTOUR)

ENDOSCOPE APPARATUS USING CURVATURE OF FIELD

RELATED APPLICATIONS

This application claims the priority of Japanese Patent Application No. 2000-41679 filed Feb. 18, 2000, and Japanese Patent Application No. 2000-85972 filed Mar. 27, 2000.

BACKGROUND OF THE INVENTION

1. Field of the Invention

The present invention relates to an endoscope apparatus, and more particularly to an apparatus capable of changing field curvature characteristics when an object to be observed is optically enlarged among others.

2. Description of the Prior Art

In recent years, in an electronic endoscope apparatus or the like, a movable lens for variable-power has been disposed at an objective lens system at the tip end portion of a scope to optically enlarge an image of the object to be observed. This optically enlarged image is picked up by an imaging device such as CCD (Charge Coupled Device), and a video signal (image signal) outputted from this CCD is subjected to various image processing by a processor apparatus to thereby display an enlarged image for the object to be observed on a monitor.

Figure 16A:
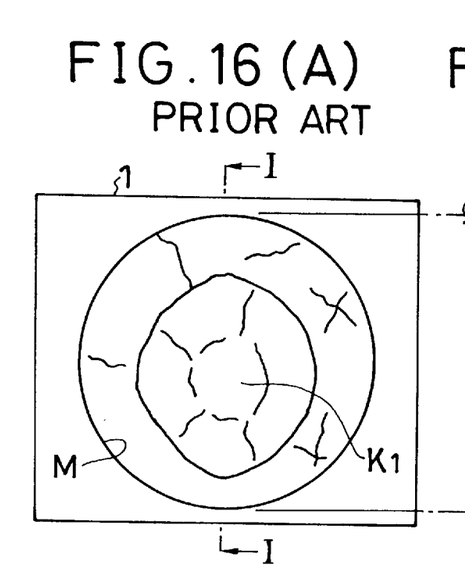
FIG. 16(A) is a view showing a state of display on a monitor for an object to be observed enlarged in a conventional electronic endoscope apparatus.
Figure 16B:
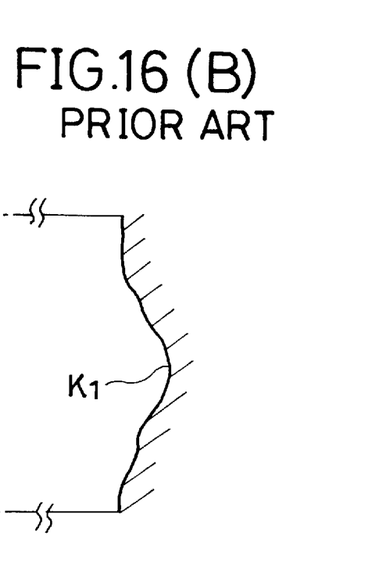
FIG. 16(B) is a view showing across section of the object to be observed of FIG. 16(A).

FIGS. 16(A) and 16(B) show an example of an enlarged display image formed by the electronic endoscope apparatus, and FIG. 16(A) shows a display on the monitor, and FIG. 16(B) shows an actual cross section showing the displayed object to be observed. This FIG. 16(A) enlarges and displays a cave-in $K_1$ of a diseased part within a circular mask M of a monitor 1, and a variable-power mechanism in the endoscope is adapted to allow a watched part to be observed by image enlargement by 70 to 100 times.

BRIEF SUMMARY OF THE INVENTION

Object of the Invention

In an objective lens system of the endoscope, however, when a particularly uneven part is enlarged, astigmatism, curvature of field or the like may throw a peripheral part or a central part out-of-focus. For example, a case of FIGS. 16(A) and 16(B) will be explained. When the central part of an enlarged cave-in $K_1$ is in focus, the periphery part goes out of focus, and when the peripheral part of the cave-in $K_1$ is in focus, the central part goes out of focus, and the entire image may not uniformly in focus. In such a state, there is the inconvenience that particularly in a freeze-frame picture to be photographed for recording, any completely satisfactory image cannot be obtained.

Also, in the above-described enlarged image for the uneven part, it is comparatively difficult to accurately grasp what degree the depth of the recessed part, the height of the protruded part, or the like is, and if height (difference) information on this unevenness could be provided, it would be exceedingly useful to diagnose, and to deal with the watched part among others.

The present invention has been achieved in the light of the above described problems, and is aimed to provide an endoscope apparatus capable of obtaining an image by attaining excellent entire focus especially during enlargement correspondingly to a shape of unevenness or the like of the object to be observed through the use of field curvature characteristics of the lens, and of obtaining information on differences in height of the uneven shape.

SUMMARY OF THE INVENTION

In order to attain the above described object, there is, according to the present invention, provided an endoscope apparatus including: an objective lens group disposed at a tip end portion of the endoscope, capable of changing the field curvature characteristics (image surface curvature characteristics including astigmatism) by moving a movable lens; image surface curving means for operating so as to change the field curvature characteristics of this objective lens group; and driving means for driving the movable lens on the basis of the operation of the image surface curving means.

According to the present invention, there are provided two movable lenses (or lens groups) in, for example, an objective lens group, whereby the structure is arranged so as to enable both a variable-power operation and an field curvature (characteristic change) operation. Thus, when an image surface curving switch disposed in an operating unit or the like is operated, the movable lens can be driven by an actuator or the like to thereby change the field curvature characteristics. This field curvature can be caused to occur in an under direction or in an over direction with respect to a reference plane, and it becomes possible to attain focus in accordance with a shape of the recessed part by an operation in the Under direction, or in accordance with a shape of the protruded part by an operation in the Over direction.

According to another aspect of the present invention, there is provided an endoscope apparatus, including: an objective lens group, disposed at the tip end portion of the endoscope, capable of changing the field curvature characteristics by moving a movable lens; driving means for driving a movable lens for field curvature of this objective lens group; judging means for dividing an imaging area for the objective lens group into a plurality and judging whether or not the central part and the peripheral part are in focus within a predetermined range by comparing information from these divided areas; and a control circuit for executing various control on the basis of output from this judging means.

According to the another aspect of the present invention, it is compared, by comparing means, whether or not the central part and the peripheral part are in focus and this focusing or defocusing, that is, the focused state is supplied to the control circuit. This control circuit outputs, for example, a static image when the whole is in a focused state. That is, when a freeze switch is depressed, no static image is outputted if the central part and the peripheral part are not in focus, but the freeze-frame picture can be displayed on the monitor and recorded only when in focus. Also, this information on the focused state may be displayed on the monitor or the like, and be notified by another means.

According to a further aspect of the present invention, there is provided an endoscope apparatus, including: an objective lens group, disposed at the tip end portion of the endoscope, capable of changing the field curvature characteristics by moving a movable lens; driving means for driving a movable lens for field curvature of this objective lens group; operating means for operating height (difference) information of the image central part to the peripheral part from an amount of field curvature changed by the objective lens group; and output means for outputting information on differences in height obtained by this operating means.

In the further aspect of the present invention, there can be provided display control means for displaying the information on differences in height obtained by the operating means on the monitor, and contour information can be displayed as the information on differences in height.

According to the another aspect of the present invention, focus is attained in accordance with the shape of the recessed part by an operation of the field curvature characteristics in the Under direction, or in accordance with the shape of the protruded part by the operation in the Over direction. An amount of field curvature when the protruded part or the recessed part is in focus can be grasped from a state of movement of the movable lens, and information on differences in height of the central part and the peripheral part of the protruded part or the recessed part can be operated from this amount of field curvature. This information on differences in height is caused to display on the monitor in, for example, the sectional shape and height difference value, or contour and height difference value by output means or the display control means and can be outputted to equipment such as a printer.

Even in this case, there is provided judging means for dividing an imaging area for the objective lens group into a plurality and judging whether or not the central part and the peripheral part are in focus within a predetermined range by comparing information from these divided areas, and when the central part and the peripheral part are in focus within a predetermined range on the basis of judgment by this judging means, the information on differences in height is preferably displayed, whereby it is possible to maintain accurate information on differences in height.

DETAILED DESCRIPTION OF THE PREFERRED EMBODIMENTS

First Embodiment

Figure 1:
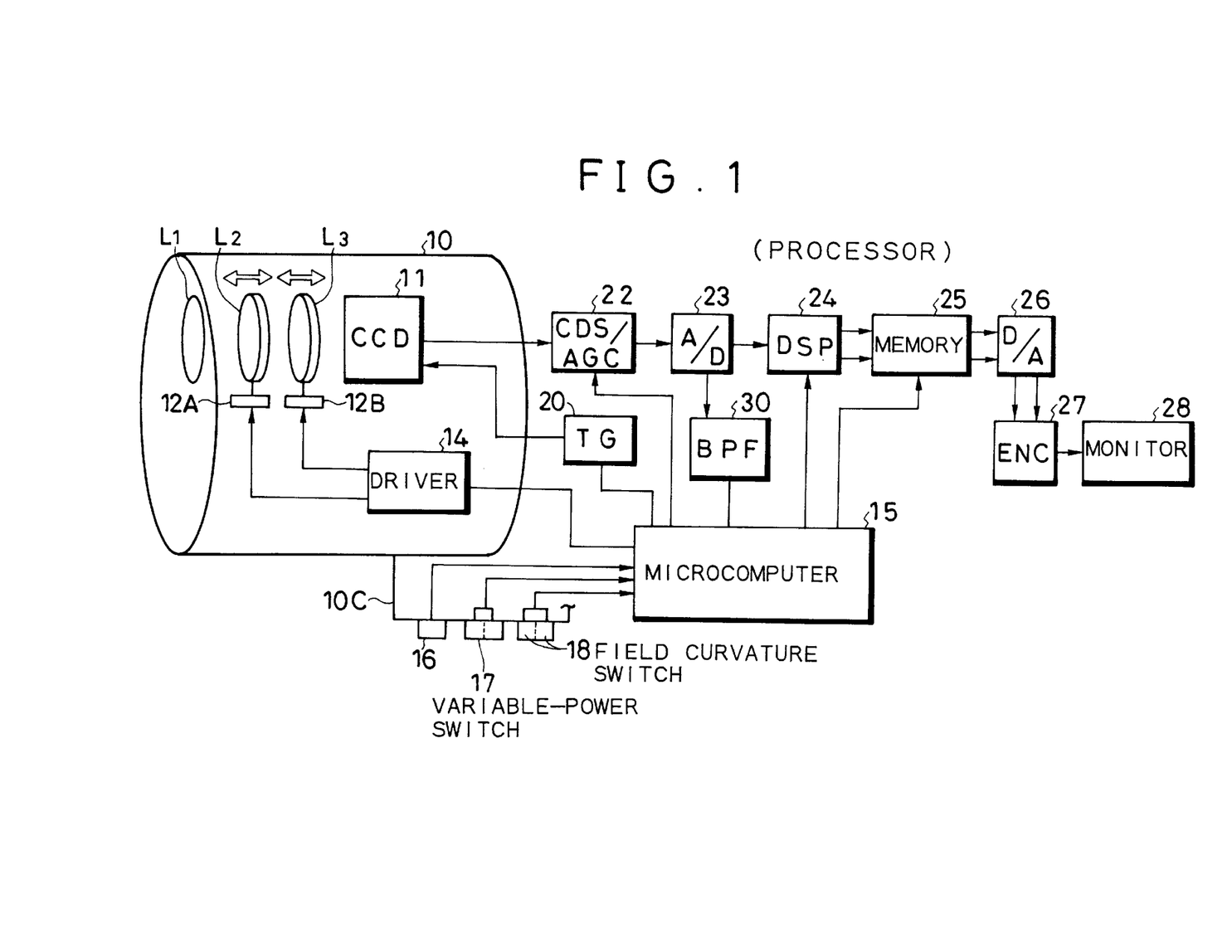
FIG. 1 is a block diagram showing a configuration of an electronic endoscope apparatus according to a first embodiment of the present invention.
Figure 2:
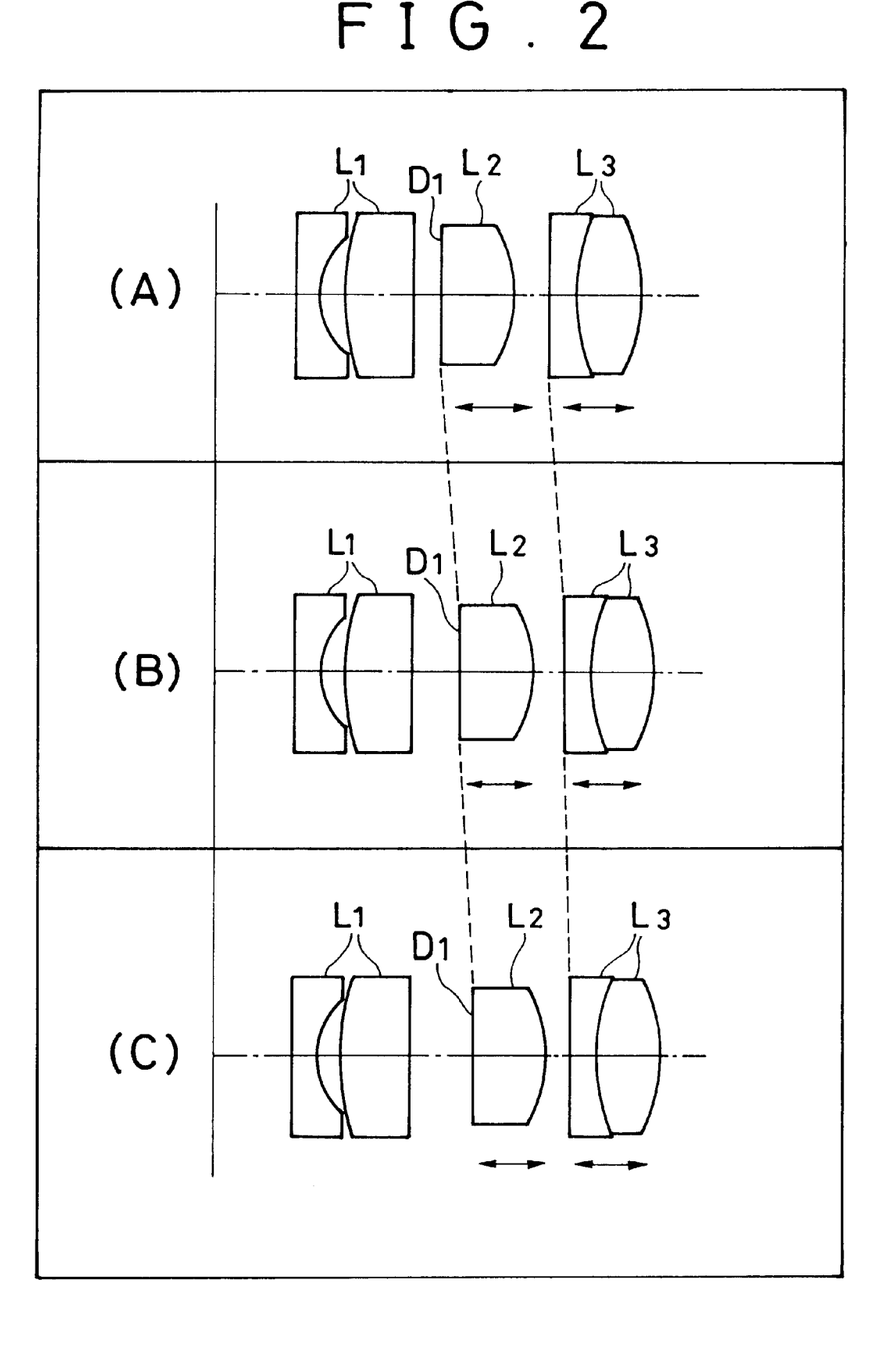
FIGS. 2(A) to 2(C) are views showing configurations of an objective lens group according to the embodiment and its operating state.

FIG. 1 shows a configuration of an electronic endoscope apparatus according to a first embodiment, and FIGS. 2(A) to 2(C) show configurations of the objective lens group of FIG. 1. In FIG. 1, at the tip end portion of an electronic scope (electronic endoscope) 10, there are provided an objective lens group (the left side of the figure is the object side) comprising a first lens (group) $L_1$, a second lens (group) $L_2$, and a third lens (group) $L_3$, and CCD11 as an imaging device, and this objective lens group utilizes so-called floating, and can be made into such a configuration as shown in, for example, FIG. 2.

As shown in FIGS. 2(A) to 2(C), the first lens $L_1$ comprises two lenses: an observation window lens (flat concave) on the left side and a flat convex lens, and is disposed as a fixed lens, the second lens $L_2$ is one sheet of flat convex lens for mainly performing a variable-power function, and the third lens $L_3$ comprises two lenses: a flat concave lens for mainly changing the field curvature characteristics and a both-convex lens, and both are disposed as a movable lens. In this respect, a diaphragm $D_1$ is integrally mounted to the front side of the second lens $L_2$. In this objective lens group, both the second lens $L_2$ and the third lens $L_3$ are caused to relatively move in the optical axis direction, whereby it is possible to scale the image and to cause field curvature.

In FIG. 1, the second lens $L_2$ is provided with an actuator 12A, and the third lens $L_3$ is provided with an actuator 12B. As these actuators 12A and 12B, various linear actuators such as a piezo-electric actuator and an electrostatic actuator, or the configuration, in which a linear transmission member is rotationally driven by a motor to convert this rotary motion into a linear motion of the lens $L_2$, $L_3$ as disclosed in Japanese Patent Application No. 11-75262 or the like, can be used. A microcomputer 15 is connected to these actuators 12A and 12B through a driver 14, and a variable-power operation and an field curvature operation are executed under the control of this microcomputer 15.

Also, in an operating unit 10C of the electronic scope 10 or the like, there are disposed a freeze switch 16 for outputting a static image or the like, a variable-power switch 17 for operating in a Near direction and a Far direction respectively, and an field curvature switch 18 (two operations) for operating in the Under direction and the Over direction respectively, and these operating signals are outputted to the microcomputer 15. Therefore, the microcomputer 15 is capable of controlling so as to enlarge and reduce an image through a control signal from the variable-power switch 17, and changing the field curvature characteristics in the Under (a focal position of the outer peripheral part moves toward the object side with respect to the center) direction and in the Over (the focal position of the outer peripheral part moves toward a side opposite to the object with respect to the center) direction through a control signal from the field curvature switch 18.

FIGS. 3(A) to 3(C) show characteristics of various aberrations to be obtained by the objective lens group of FIGS. 2(A) to 2(C), and FIGS. 3(A) to 3(C) correspond to the lens positions in FIGS. 2(A) to 2(C). FIG. 4 conceptually shows synthetic characteristics of field curvature, and represents a focal position of CCD 11 from the central point of the imaging surface in a vertical V direction (height direction). When the second lens $L_2$ and the third lens $L_3$ are relatively moved by a predetermined amount as shown in, for example, FIGS. 2(A) to 2(C), any amount of field curvature can be caused to occur from Under (characteristic Ja), in which the image surface falls down on the object side, to Over (characteristic Jz), in which the image surface falls down on the opposite side, and this characteristic can be changed.

On the other hand, in FIG. 1, a timing generator (TG) 20 for supplying a signal for reading out a video signal to the CCD 11 is connected to the processor apparatus, and as a video signal processing system, a CDS (Correlated Double Sampling)/AGC (Automatic Gain Control) circuit 22, an AD converter 23, a DSP (Digital Signal Processor) 24 for performing various digital processing such as white balance, gamma correction and profile correction, a frame memory 25 for storing an image once, a DA converter 26, and an encoder (ENC) 27 for adjusting a video signal to the form of an indicator for outputting are disposed in the processor apparatus or the like. A video signal of the object to be observed to be outputted from the encoder 27 is supplied to a monitor 28.

Also, in the example concerned, it is judged whether or not the central part and the peripheral part of an image or an image plane are in focus, a band pass filter (BPF) 30 for extracting a high-pass component (contrast data for the edge portion) of the video signal for this judgment is provided in the latter part of the AD converter 23, and output from the BPF30 is supplied to the microcomputer 15. This microcomputer 15 performs various control of the apparatus functions, and judges the above described focusing state.

Figure 6:
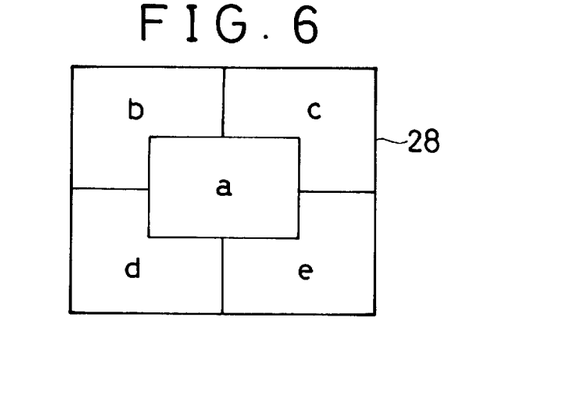
FIG. 6 is a view showing divided areas to be compared by focus judging means for an entire image.

That is, as shown in FIG. 6, the image (image plane) area is divided into a central part a and four peripheral parts b, c, d and e, and a high-pass component of the above described video signal in these divided areas a to e is extracted.

When high-pass components in, for example, all areas (may be any of a and b to e, and not be all) exceed a reference value, it is judged that the entire image plane is in focus. In the example concerned, in the case where a static image is selected by operating the freeze switch 16, control is performed so as to output the freeze-frame picture only when this focusing state is judged.

The first embodiment is configured as described above, and its operation will be described. In the apparatus concerned, the object to be observed is grasped by the above described objective lens group ($L_1$ to $L_3$), and when an image of this object to be observed is picked up by the CCD11, the video signal is read out from a read-out signal from the timing generator 20, and after subjected to the correlated double sampling and the amplification processing in the CDS/AGC circuit 22, is subjected to various processing as a digital signal in the DSP24. The video signal thus formed is outputted into the monitor 28 through the encoder 27 to thereby display a moving image for the object to be observed on the monitor 28.

When a variable-power switch 17 of the electronic scope operating unit 10C is operated, the second lens $L_2$ and the third lens $L_3$ are move-controlled by the microcomputer 15, the driver 14 and the actuator 12A, 12B, an enlarged image is obtained from a basic image by focusing in the Near direction, a reduced image in the direction that returns to the basic image is obtained by focusing in the Far direction, and these images are picked up by the CCD 11. During enlargement in the Near direction, however, the peripheral part may not be in focus due to the field curvature characteristics in the object to be observed in which there exists unevenness.

At times like this, the peripheral part can be brought into focus by operating the field curvature switch 18. That is, when this field curvature switch 18 is operated in the Over direction, the second lens $L_2$ and the third lens $L_3$ are move-controlled by the actuator 12A, 12B as shown in FIGS. 2(A) to 2(C), whereby the field curvature characteristics, which change from a focal position (Ja) of the Under of FIG. 4 to a focal position (Jz) of the Over, is imparted. Also, when operated in the Under direction, the field curvature characteristics, which change from the focal position (Jz) of the Over to the focal position (Ja) of the Under, can be set by a moving operation of the lenses $L_2$ and $L_3$ in the opposite direction to the above described operation.

Figure 5A:
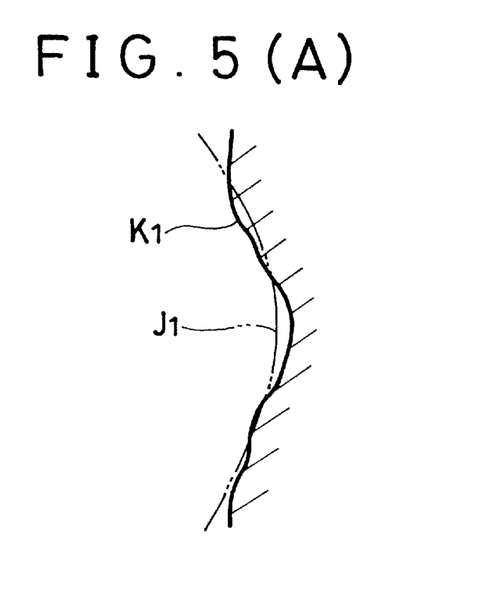
FIGS. 5(A) and 5(B) are views showing relationship between an uneven shape and field curvature characteristics capable of occurring of an object to be observed.
Figure 5B:
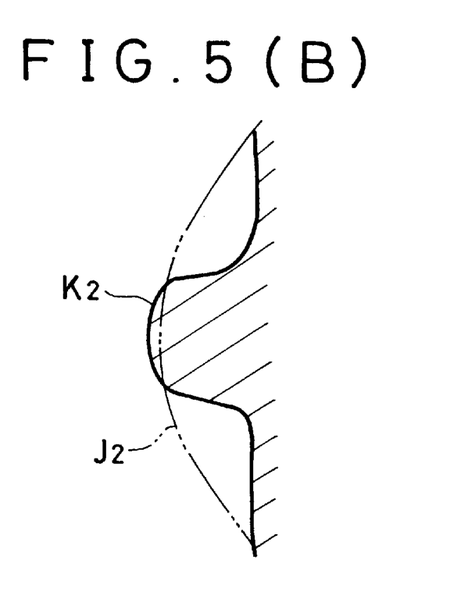

For example, if the object to be observed is the cave-in $K_1$ as shown in FIG. 5(A), the curvature of field of the characteristic $J_1$ of the Under is imparted, whereby focusing suitable for the shape of the cave-in $K_1$ is performed, and if the object to be observed is the protruded part $K_2$ as shown in FIG. 5(B), the curvature of field of the characteristic $J_2$ Of the Over is imparted, whereby focusing suitable for the shape of the protruded part $K_2$ is performed.

On the other hand, when the freeze switch 16 of the electronic scope operating unit 10C is operated, formation of a freeze-frame picture is controlled by the microcomputer 15, and a video signal when the freeze switch 16 is depressed is written in the frame memory 25, whereby the static image is displayed on the monitor 18, and this static image is also outputted to a recording device for hard copy or the like.

In the example concerned, when this static image is outputted, the microcomputer 15 judges whether or not the entire image is in focus on the basis of the high-pass component inputted from the BPF30.

Figure 7:
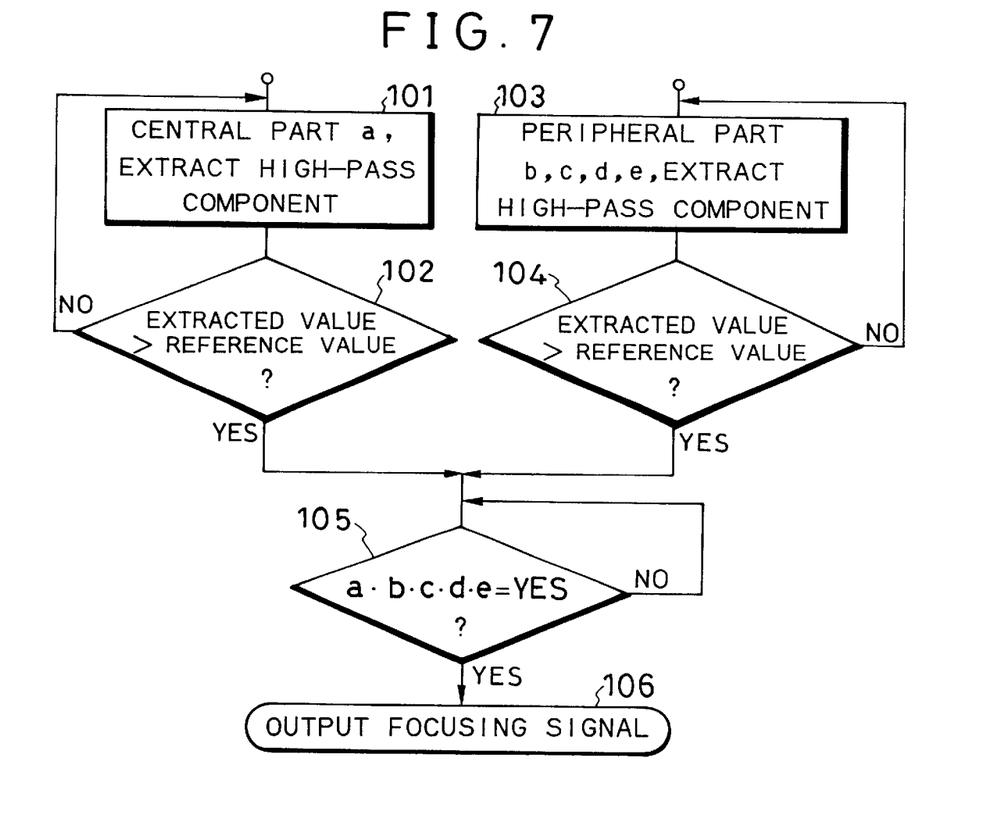
FIG. 7 is a flow chart showing a focus judging operation in a microcomputer according to the embodiment.

FIG. 7 shows an operation of the microcomputer 15 at this time, and in Step 101, a high-pass component of the image central part a explained in FIG. 6 is extracted, and it is compared by the next Step 102 whether or not this extracted value is larger than a reference value (extracted value>reference value). On the other hand, in Step 103, high-pass components in the image peripheral parts b, c, d, e of FIG. 6 are extracted, and it is compared by next Step 104 whether or not this extracted value is larger than the reference value (extracted value>reference value). Next, in Step 105, it is judged whether or not comparative output from the areas a, b, c, d and e are all YES (a·b·c·d·e=YES?), and if YES, a focusing signal (entirely focused signal) is outputted (Step 106).

When a focusing signal is outputted in the Step 106, the microcomputer 15 allows a static image to be outputted. That is, if this focusing signal is not obtained even though the freeze switch 16 has been depressed, any static image will be caused not to be outputted to thereby improve the image quality of the static image.

Also, the structure can be also arranged such that the focusing state of the entire image is displayed (or notified) on a monitor or an operating panel or the like of the processor apparatus. In the case where this focusing state is displayed, the output is not limited when the static image is formed by the microcomputer 15, and it maybe possible for the operator to depress the freeze switch 16 by using the same control as the conventional one, and confirming the focusing state displayed on the monitor.

As described above, according to the first embodiment, there are provided an objective lens group for changing the field curvature characteristics, and an field curvature switch for operating an amount of change in field curvature, and field curvature is caused to occur in contrast with ordinary cases through driving means by operating this switch. Therefore, field curvature of the Under or the Over is imparted in accordance with the shape such as unevenness of the object to be observed, whereby particularly a blurred state in the peripheral part during enlargement is eliminated, and it becomes possible to obtain an entirely excellent image.

Second Embodiment

Figure 8:
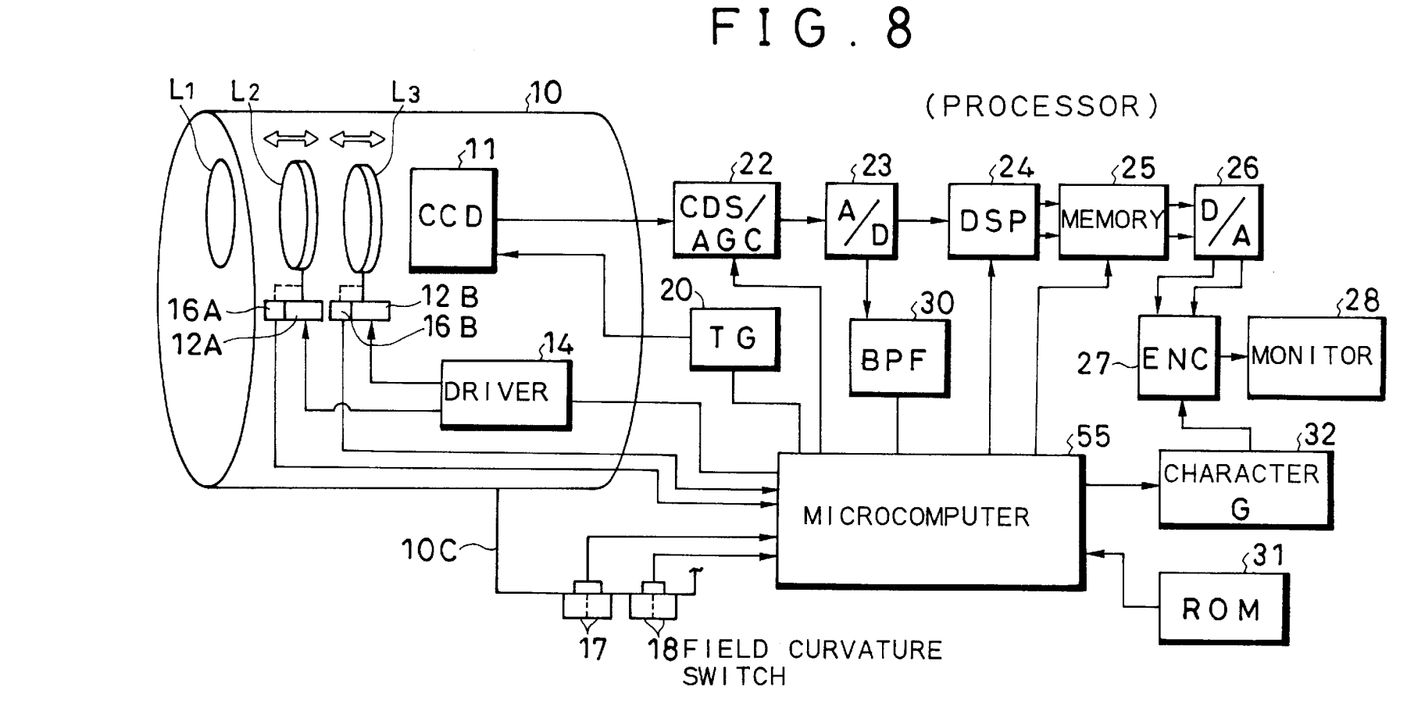
FIG. 8 is a block diagram showing a configuration of an electronic endoscope apparatus according to a second embodiment of the present invention.

FIG. 8 shows a configuration of an electronic endoscope apparatus according to a second embodiment, and even in this second embodiment, there is used such an objective lens group as shown in FIG. 2, using so-called floating. In FIG. 8, at the tip end portion of the electronic scope 10, there are provided a lens (group) $L_1$, $L_2$, $L_3$ and CCD11. Also, there are provided various linear actuators and actuators 12A, 12B using linear transmission members, and a microcomputer 55 is connected to these actuators 12A, 12B through a driver 14, and the variable-power operation and the image surface curving operation are executed under the control of the microcomputer 55. This microcomputer 55 performs various control of the apparatus functions in addition.

Also, in an operating unit 10C of the electronic scope 10 or the like, there are disposed a variable-power switch 17 and an field curvature switch 18, and these operating signals are outputted to the microcomputer 55. Thereby, the image is enlarged and reduced, and the field curvature characteristics can be, as described in FIG. 4, generated in the Under direction, in which a focal position of the outer peripheral part moves toward the object side with respect to the center and in the Over direction, in which the focal position of the outer peripheral part moves toward a side opposite to the object with respect to the center.

Encoders 16A and 16B for detecting a moving position of the second lens $L_2$ and the third lens $L_3$ are provided, and the microcomputer 55 specifies the enlargement ratio on the basis of output from the encoder 16A, 16B, and computes an amount of field curvature which is currently occurring.

Figure 3:
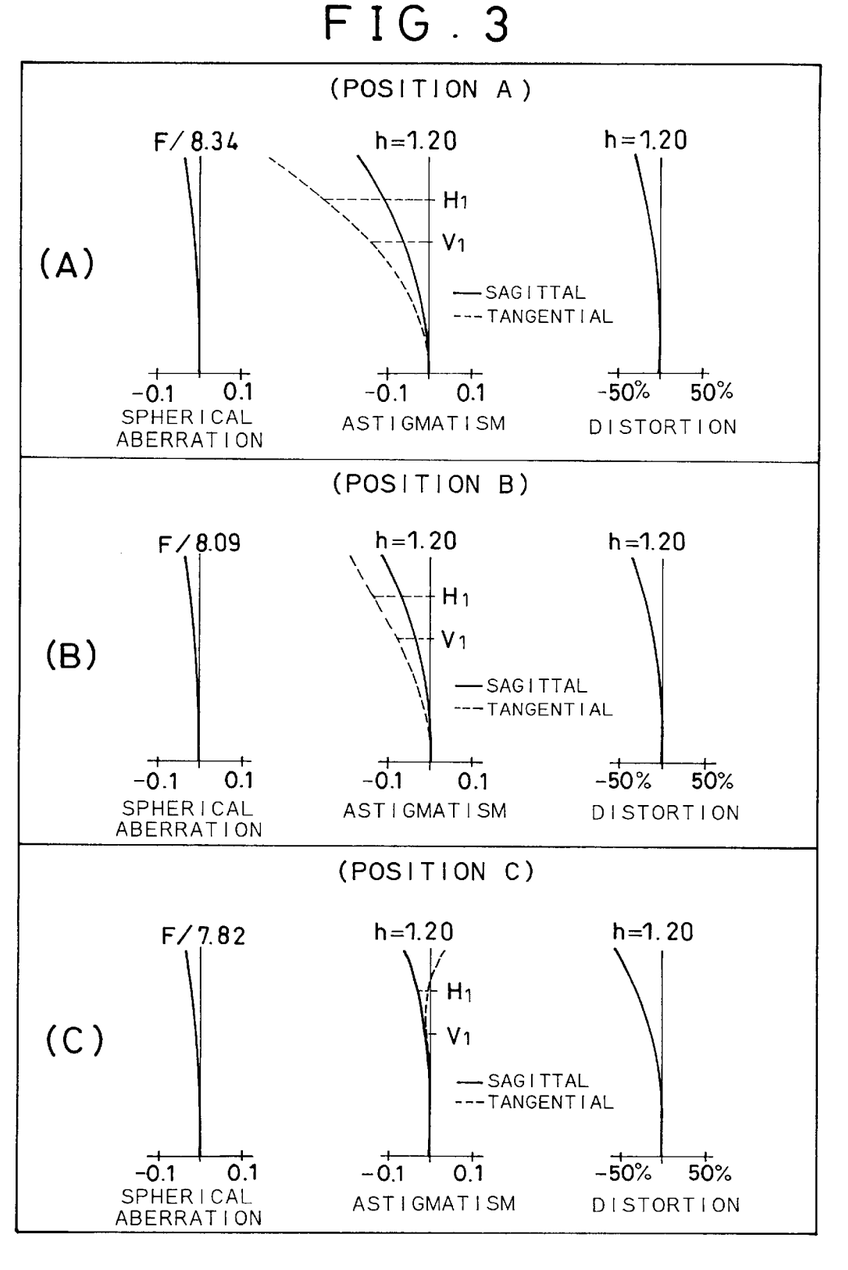
FIGS. 3(A) to 3(C) are graphs showing various aberrations of the objective lens group of FIG. 2.
Figure 4:
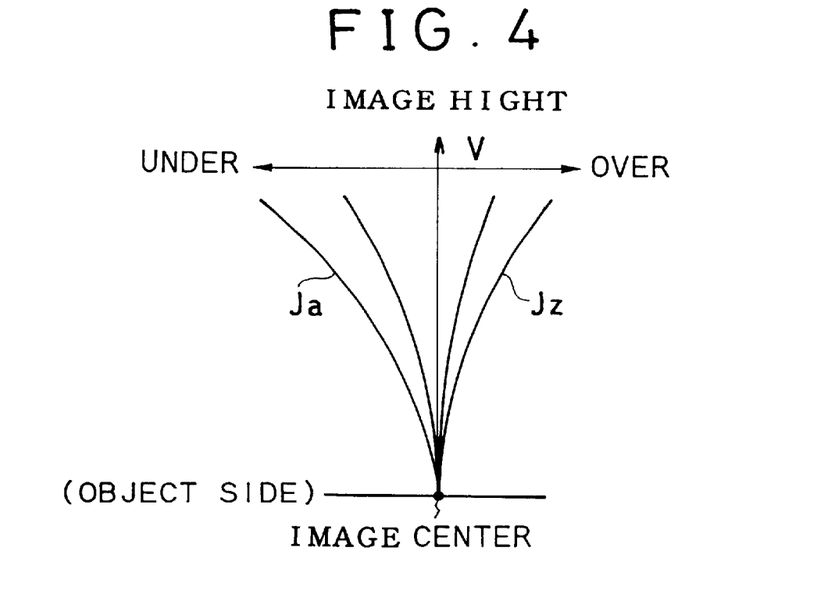
FIG. 4 is a graph showing a state (amount) of an field curvature which occurs by means of the objective lens group according to the first embodiment.
Figure 9:
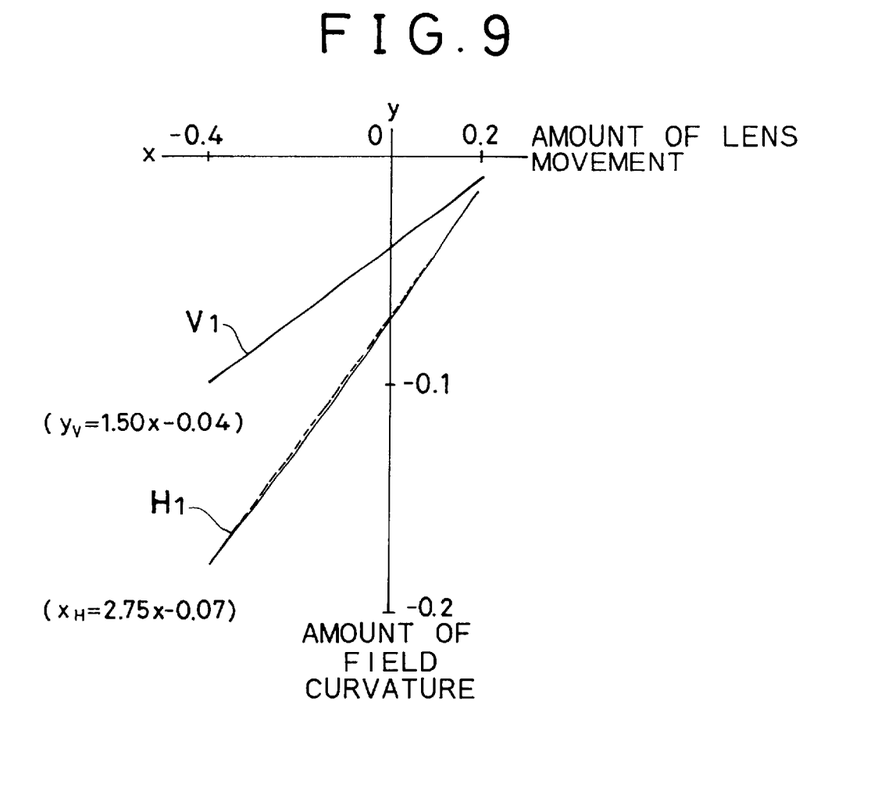
FIG. 9 is a view showing relationship between an amount of movement of a lens and an amount of field curvature in an objective lens group according to the embodiment.

FIG. 9 shows relationship of an amount (y) of field curvature to an amount (x) of movement of the third lens $L_3$ and an arithmetic expression for the image plane at the up-and-down ends (vertical direction) $V_1$ can be approximated by $y_v=1.50x-0.04$ (first arithmetic expression) as shown in, for example, the graph on astigmatism of FIG. 3, assuming that an average image surface of sagittal plane and tangential plane corresponding to 60 percent of the image light is grasped. Also, an arithmetic expression for the image plane at the right-and-left ends (horizontal direction) $H_1$ can be approximated by $y_H=2.75x-0.07$ (second arithmetic expression) as shown in, for example, the graph on astigmatism of FIG. 3, assuming that an average image surface of sagittal plane and tangential plane corresponding to 80 percent of the image light is grasped.

Amounts of field curvature at the up-and-down ends $V_1$ and the right-and-left ends $H_1$ when the center of the image plane is y=0 can be obtained from the first and second arithmetic expressions, and a difference in height between the central part and the peripheral part can be obtained from this amount of field curvature and an enlargement ratio at this time. Also, the arithmetic expression can be obtained correspondingly to an image height (h), and if differences in height in plural points are computed by using arithmetic expressions in plural points, contour data will be able to be obtained.

In FIG. 8, a configuration of the timing generator (TG) to the monitor 28 becomes the same as in the first embodiment. In the second embodiment, in order to display information on a difference in height based on the amount of field curvature, there are provided a ROM (Read Only Memory) 31 and a character generator 32. That is, in the ROM 31, there are stored data on the amount of field curvature sampled in accordance with an image height to be obtained from the position of the third lens $L_3$ by the first and second arithmetic expressions, and data on a difference in height represented into a table in response to an enlargement ratio to be judged from the position of the second lens $L_2$, and these data are read out by the microcomputer 55, and the character generator 32 generates such information picture on a difference in height as shown in FIGS. 10 to 12(A) and 12(B) on the basis of this data on differences in height.

The microcomputer 55 judges whether or not the central part and the peripheral part of an image or an image plane are in focus, as in the first embodiment, and there is provided a band pass filter (BPF) 30 for extracting a high-pass component of a video signal for this judgment. That is, as shown in FIG. 6, a high-pass component of the video signal of the divided areas a to e is extracted, and for example, when high-pass components in all the areas exceed the reference value, it is judged that the entire image plane is in focus. In the example concerned, only when this focusing state is judged, it is also possible to control so as to display the information on differences in height, and this focusing state can be only displayed on the monitor or the like.

Further, it may be possible to control so as to display the information on differences in height during an operation of the field curvature switch 18, and to dispose an operating switch for the exclusive use of displaying differences in height either in the processor apparatus or in the electronic scope 10.

The second embodiment has the above described configuration, and its operation will be described. An object to be observed is grasped by the above described objective lens group ($L_1$ to $L_3$), and a moving image of the object to be observed is displayed on the monitor 28 on the basis of an pickup image by CCD 11. By operating the variable-power switch 17, the second lens $L_2$ and the third lens $L_3$ are move-controlled, an enlarged image from a basic image is obtained by focusing in the Near direction, and a reduced image in the direction that returns to the basic image is obtained by focusing in the Far direction.

However, the peripheral part may not be in focus due to the field curvature characteristics, and at this time, the peripheral part can be brought into focus by operating the field curvature switch 18. That is, by operating the field curvature switch 18 in the Over direction, the curvature of field, which changes from the focal position (Ja) of the Under of FIG. 4 to the focal position (Jz) of the Over, is imparted, and by operating it in the Under direction, the curvature of field, which changes from the focal position (Jz) of the Over to the focal position (Ja) of the Under, is set. Even if it is the cave-in $K_1$ of FIG. 5(A) or the protruded part $K_2$ of FIG. 5(B), focusing suitable for their shape is performed.

When the curvature of field occurs, when the difference in height indicating switch is depressed, or the like, the microcomputer 55 reads out data on differences in height from the ROM 31 on the basis of data on positions (outputs from encoder 16A, 16B) of the second lens $L_2$ and the third lens $L_3$ to supply this data on differences in height to the character generator 32. This character generator 32 forms a difference in height indicating picture for the present image of the object to be observed together with values of differences in height for outputting to display this difference in height indicating picture on the monitor 28.

Figure 10:
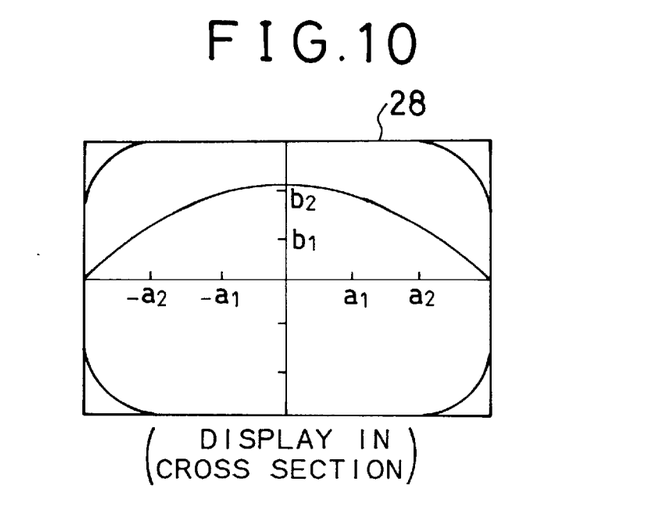
FIG. 10 is a view when information on differences in height of a protruded part of an object to be observed on a monitor is displayed in a cross section.

That is, FIG. 10 shows information on differences in height of the protruded part in cross section, and in this case, actual dimensions such as height $b_1$, $b_2$ with a sectional shape of the protruded part and the peripheral part as the reference (0) and length $a_1$, $a_2$ or the like in the horizontal direction are displayed on the monitor 28.

Figure 11:
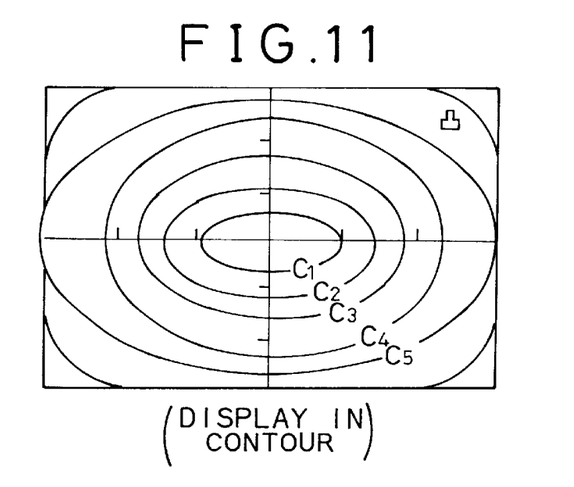
FIG. 11 is a view when information on differences in height of a protruded part of an object to be observed on a monitor is displayed in a contour.

FIG. 11 displays information on differences in height of the protruded part in contour (bird's-eye display), and in this case, dimensions such as height $c_1$ to $c_5$ with the contour shape and the peripheral part as the reference are displayed.

Figure 12A:
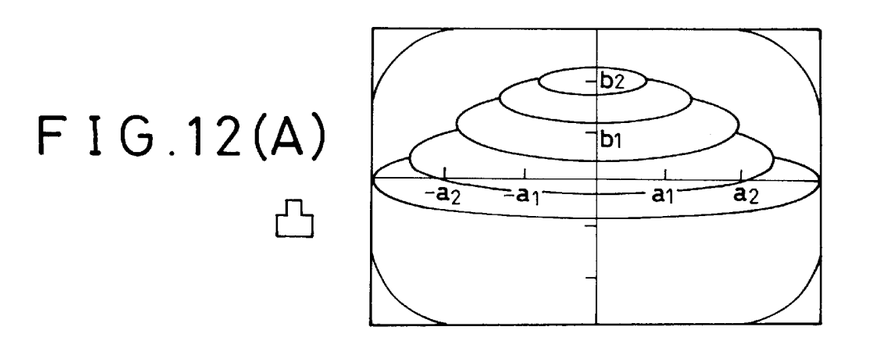
FIG. 12(A) is a view when information on differences in height of a protruded part of an object to be observed on a monitor is displayed three-dimensionally.
Figure 12B:
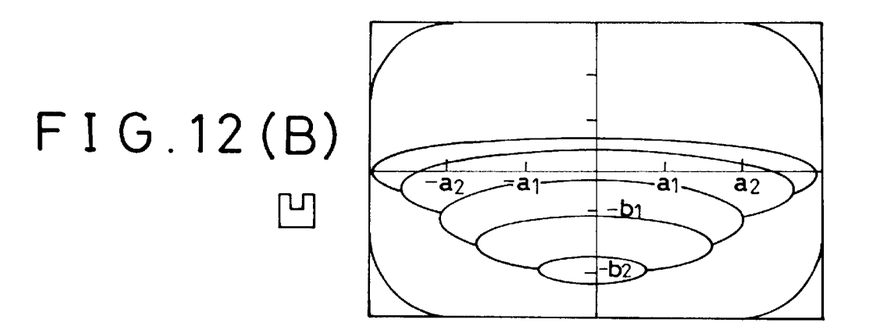
FIG. 12(B) is a view when information on differences in height of a recessed part of an object to be observed on a monitor is displayed three-dimensionally.

FIGS. 12(A) and 12(B) three-dimensionally display a protruded part or a recessed part, and in this case, dimensions such as height $b_1$, $b_2$ with the three-dimensional shape and the peripheral part as the reference like the protruded part of FIG. 12(A) and the recessed part of FIG. 12(B), and length $a_1$, $a_2$ in the horizontal direction are displayed on the monitor 28. In this respect, these differences in height indicating pictures are displayed superimposed on an image of the object to be observed. Also, the information on differences in height can be also outputted to equipment such as printers.

A microcomputer 55 in the example concerned judges, on the basis of a high-pass component inputted from the BPF30, whether or not the entire image is in focus in accordance with the operation of FIG. 7. When a focusing signal is outputted in Step 106 of FIG. 7, the microcomputer 55 is capable of controlling so as to allow the information on differences in height to be displayed. According to this, when no focusing signal is obtained, the information on differences in height is not displayed, whereby the accuracy of the information can be secured.

Figure 13:
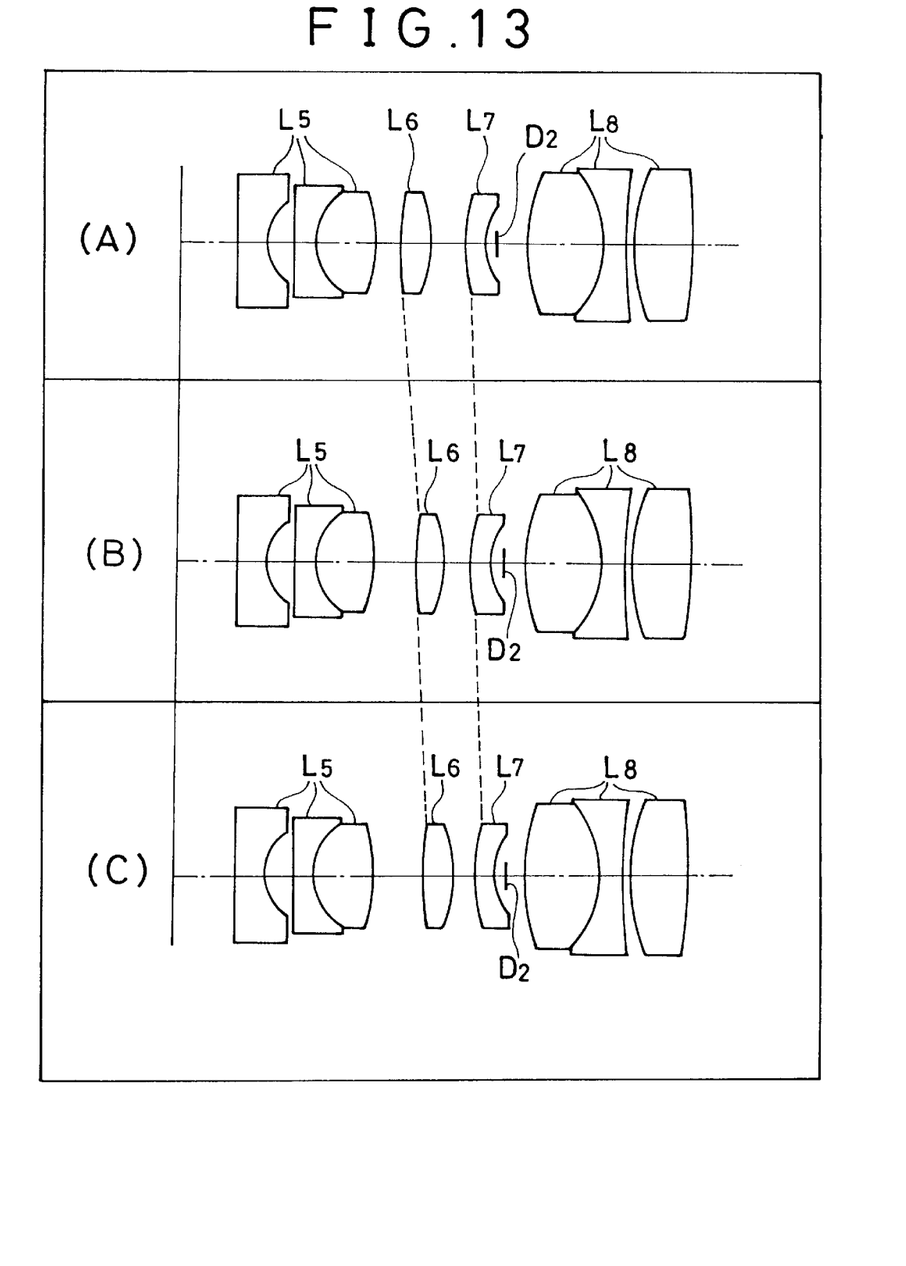
FIGS. 13(A) to 13(C) are views showing configurations of another objective lens group according to the embodiment.

FIG. 13 shows a configuration of another objective lens group having a different configuration from FIG. 2. This another objective optical system is configured by a first lens (group) $L_5$, a second lens $L_6$, a third lens $L_7$ and a fourth lens $L_8$ (group), and the first lens $L_5$ is a fixed lens comprising three lenses: an observation window lens (flat concave) on the left side, a flat concave lens and a both convex lens. On the other hand, the second lens $L_6$ as a movable lens is one sheet of both convex lens, the third lens $L_7$ as a movable lens comprises one sheet of meniscus lens whose concave surface faces the image side, and the fourth lens $L_8$ is a fixed lens comprising three lenses: a both-convex lens, a both-concave lens and a both-convex lens. In this respect, a diaphragm $D_2$ is integrally mounted to the rear side of the third lens $L_7$. Even in such an objective optical system, both the second lens $L_6$ and the third lens $L_7$ are caused to relatively move in the optical axis direction, whereby a variable-power image can be obtained and the curvature of field can be changed.

Figure 14:
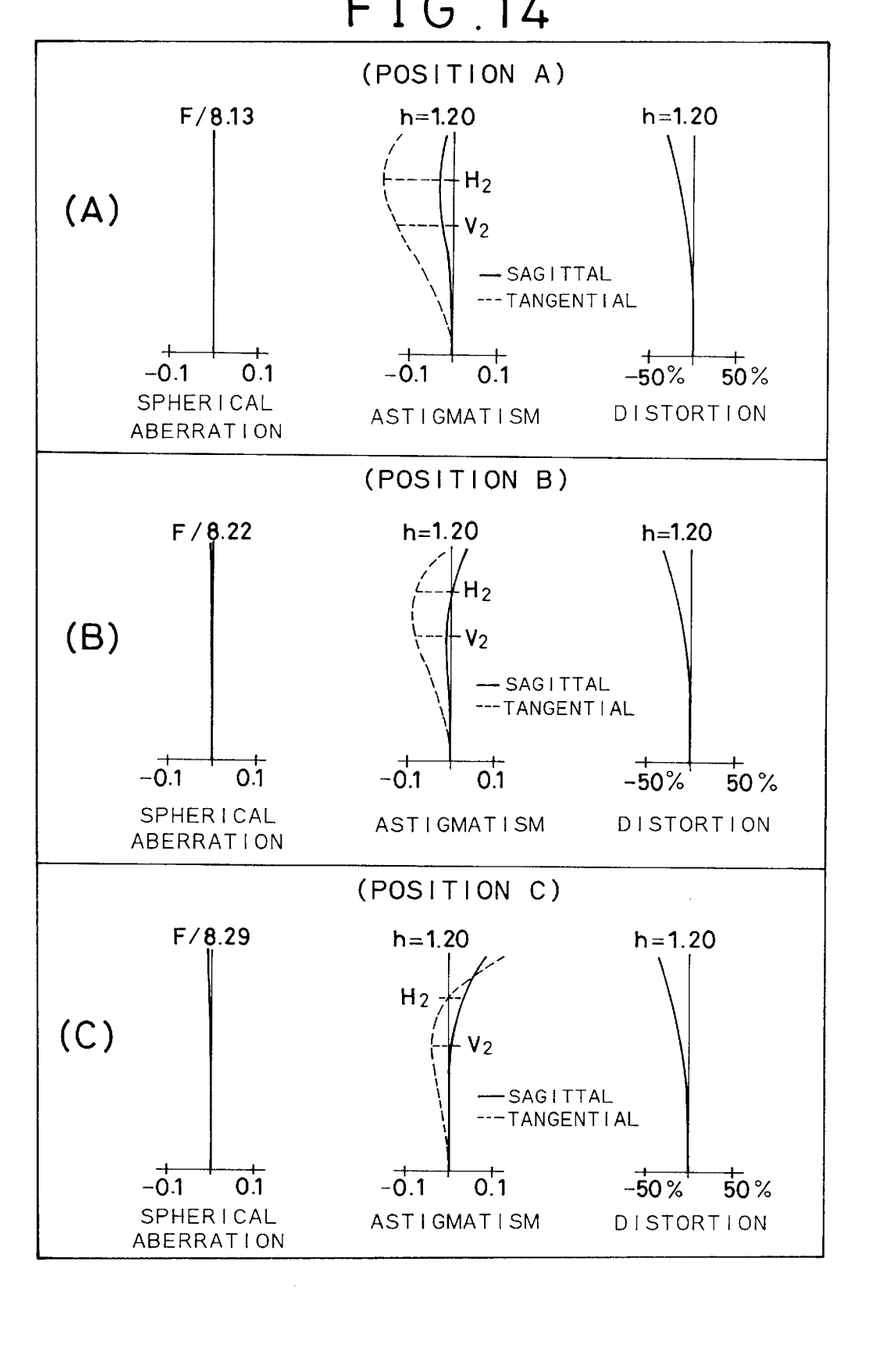
FIGS. 14(A) to 14(C) are graphs showing various aberrations of another objective lens group.
Figure 15:
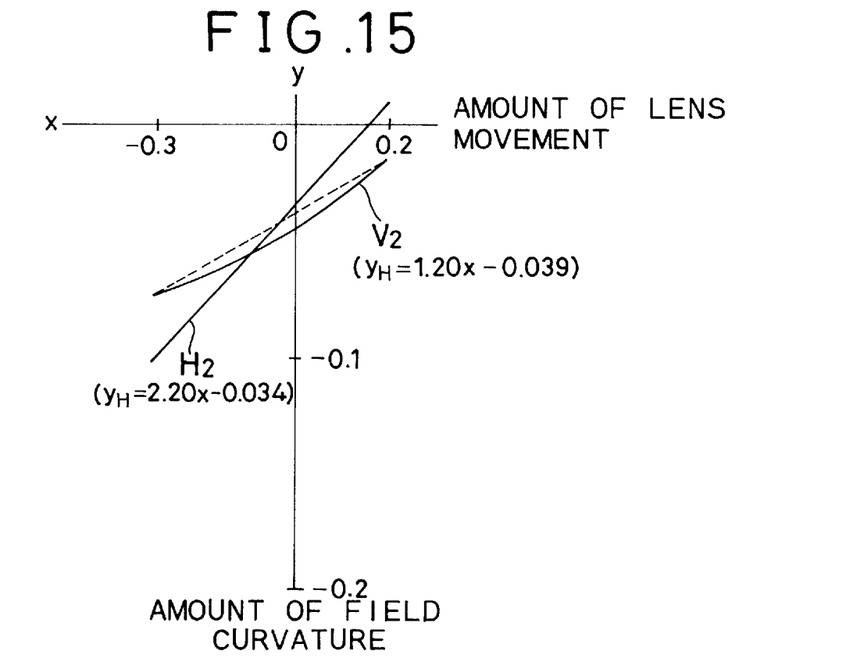
FIG. 15 is a view showing relationship between an amount of movement of a lens and an amount of an field curvature in another objective lens group.

FIGS. 14(A) to 14(C) show various aberrations of another objective lens group of FIG. 13, and in an objective lens group having such characteristics, the arithmetic expression shown in FIG. 15 can be obtained. That is, FIG. 15 shows the amount (y) of field curvature to the amount (x) of movement of the third lens $L_3$, and even in this case, an arithmetic expression for the image plane at the up-and-down ends $V_2$ can be approximated by $y_v = 1.20x - 0.039$ (third arithmetic expression) as shown in the graph on astigmatism of FIG. 14 assuming that an average image surface of sagittal plane and tangential plane corresponding to 60 percent of the image light is grasped. Also, an arithmetic expression for the image plane at the right-and-left ends $H_2$ can be approximated by $y_H = 2.20x - 0.034$ (fourth arithmetic expression) as shown in, for example, the graph on astigmatism of FIG. 3 assuming that an average image surface of sagittal plane and tangential plane corresponding to 80 percent of the image light is grasped.

As described above, according to the second embodiment, information on differences in height of the image central part with respect to the peripheral part is determined from the amount of field curvature, this information on differences in height is displayed on the monitor, and it is arranged that the information on differences in height can be outputted to another equipment. Therefore, the blurred state in the peripheral part of the uneven portion in the object to be observed during enlargement cannot only be eliminated, but also it becomes possible to obtain information on differences in height of an uneven shape, and information useful for diagnosis, treatment or the like for a watched part can be provided.

What is claimed is:

1. An endoscope apparatus, comprising:
   an objective lens group disposed at a tip end portion of an endoscope, capable of changing field curvature characteristics by moving a movable lens;
   an imaging device for picking up an observation object through said objective lens group;
   image surface curving means for operating so as to change the field curvature characteristics of said objective lens group;
   driving means for driving said movable lens on the basis of an operation of said image surface curving means;
   judging means for dividing an imaging area of said imaging device into a plurality of areas and judging whether or not a central part and a peripheral part are in focus within a predetermined range by comparing video signal information of divided imaging areas; and
   a control circuit for executing various control on the basis of output from said judging means.

2. The endoscope apparatus according to claim 1, wherein an field curvature lens is installed into said objective lens group together with a variable-power lens for changing an image enlargement ratio to control driving of both variable-power and change of the field curvature characteristics.

3. The endoscope apparatus according to claim 1, wherein when a central part and a peripheral part are in focus within a predetermined range on the basis of judgment of said judging means, said control circuit controls so as to output a static image.

4. An endoscope apparatus, comprising:
   an objective lens group, disposed at a tip end portion of an endoscope, capable of changing field curvature characteristics by moving of a movable lens;
   an imaging device for picking up an observation object through said objective lens group;
   driving means for driving a movable lens for field curvature of said objective lens group;
   judging means for dividing an imaging area of said imaging device into a plurality of areas and judging whether or not a central part and a peripheral part are in focus within a predetermined range by comparing video signal information of divided imaging areas;
   operating means for operating information on differences in height of an image central part to a peripheral part from an amount of field curvature changed by said objective lens group; and
   output means for outputting information on differences in height obtained by said operating means, when the central part and the peripheral part are in focus within the predetermined range on the basis of judgment by said judging means.

5. The endoscope apparatus according to claim 4, further comprising display control means for picture-displaying information on differences in height obtained by said operating means on a monitor.

6. The endoscope apparatus according to claim 4, wherein contour information is displayed as said information on differences in height.

7. The endoscope apparatus, comprising:

an objective lens group disposed at a tip end portion of an endoscope, capable of changing field curvature characteristics by moving a movable lens;

image surface curving means for operating so as to change the field curvature characteristics of said objective lens group;

driving means for driving said movable lens on the basis of an operation of said image surface curving means;

wherein a field curvature lens is installed into said objective lens group together with a variable-power lens for changing an image enlargement ratio to control driving of both variable-power and change of the field curvature characteristics; and wherein when a central part and a peripheral part are in focus within a predetermined range on the basis of judgment of said judging means, said control circuit controls so as to output a static image.

8. The endoscope apparatus, comprising:

an objective lens group, disposed at a tip end portion of an endoscope, capable of changing field curvature characteristics by moving of a movable lens;

driving means for driving a movable lens for field curvature of said objective lens group;

operating means for operating information on differences in height of an image central part to a peripheral part from an amount of field curvature changed by said objective lens group; and output means for outputting information on differences in height obtained by said operating means; and further comprising display control means for picture-displaying information on differences in height obtained by said operating means on a monitor.

9. The endoscope apparatus, comprising:

an objective lens group, disposed at a tip end portion of an endoscope, capable of changing field curvature characteristics by moving of a movable lens;

driving means for driving a movable lens for field curvature of said objective lens group;

operating means for operating information on differences in height of an image central part to a peripheral part from an amount of field curvature changed by said objective lens group; and output means for outputting information on differences in height obtained by said operating means; and wherein contour information is displayed as said information on differences in height.

* * * * *